(12) United States Patent
Bouserhal et al.

(10) Patent No.: US 10,783,904 B2
(45) Date of Patent: Sep. 22, 2020

(54) DEVICE AND METHOD FOR IMPROVING THE QUALITY OF IN-EAR MICROPHONE SIGNALS IN NOISY ENVIRONMENTS

(71) Applicant: EERS GLOBAL TECHNOLOGIES INC., Montréal (CA)

(72) Inventors: Rachel E. Bouserhal, Montréal (CA); Jérémie Voix, Montréal (CA); Tiago Falk, Gatineau (CA)

(73) Assignee: EERS GLOBAL TECHNOLOGIES INC., Montreal, Québec (CA)

( * ) Notice: Subject to any disclaimer, the term of this patent is extended or adjusted under 35 U.S.C. 154(b) by 144 days.

(21) Appl. No.: 16/099,274

(22) PCT Filed: May 10, 2017

(86) PCT No.: PCT/CA2017/000115
§ 371 (c)(1),
(2) Date: Nov. 6, 2018

(87) PCT Pub. No.: WO2017/190219
PCT Pub. Date: Nov. 9, 2017

(65) Prior Publication Data
US 2019/0214038 A1    Jul. 11, 2019

Related U.S. Application Data

(60) Provisional application No. 62/460,682, filed on Feb. 17, 2017, provisional application No. 62/332,861, filed on May 6, 2016.

(51) Int. Cl.
*G10L 25/84* (2013.01)
*H04R 1/10* (2006.01)
(Continued)

(52) U.S. Cl.
CPC ............ *G10L 25/84* (2013.01); *H04R 1/1016* (2013.01); *H04R 1/1083* (2013.01); *H04R 3/005* (2013.01);
(Continued)

(58) Field of Classification Search
USPC ...................................................... 704/1–504
See application file for complete search history.

(56) References Cited

U.S. PATENT DOCUMENTS

| 6,275,806 B1 * | 8/2001 | Pertrushin ............... G10L 17/26 |
| | | 704/270 |
| 8,675,884 B2 | 3/2014 | Yehuday et al. |

(Continued)

FOREIGN PATENT DOCUMENTS

| EP | 2555189 A1 | 2/2013 |
| EP | 2843915 A1 | 3/2015 |

*Primary Examiner* — Marcus T Riley
(74) *Attorney, Agent, or Firm* — Praxis

(57) ABSTRACT

A method, and device, for enhancing speech generated from bone and tissue conduction of a user of an In-ear device in a noisy environment, the Intra-aural device having an in-ear microphone adapted to be in fluid communication with the ear canal of the user and an outer-ear microphone adapted to be in fluid communication with the environment outside the ear. The method comprises applying an adaptive filter on the in-ear microphone signal, using the outer-ear microphone signal as a reference for the ambient noise and interrupting the application of the adaptive filter to the In-ear microphone signal upon detecting speech by the user.

40 Claims, 12 Drawing Sheets

(51) Int. Cl.
*H04R 3/00* (2006.01)
*A61F 11/14* (2006.01)

(52) U.S. Cl.
CPC ..... *A61F 2011/145* (2013.01); *H04R 2410/01* (2013.01); *H04R 2460/01* (2013.01)

(56) References Cited

U.S. PATENT DOCUMENTS

| | | | |
|---|---|---|---|
| 8,682,010 B2 | 3/2014 | Macours | |
| 2003/0023444 A1* | 1/2003 | St. John | H04M 3/382 770/270.1 |
| 2007/0160243 A1 | 7/2007 | Dijkstra et al. | |
| 2011/0125063 A1* | 5/2011 | Shalon | A61B 5/1112 600/590 |
| 2011/0135106 A1* | 6/2011 | Yehuday | H04R 3/005 381/71.6 |
| 2011/0293105 A1* | 12/2011 | Arie | H04R 1/1083 381/71.11 |
| 2015/0170633 A1* | 6/2015 | Nakagawa | G10K 11/175 381/71.6 |
| 2019/0214038 A1* | 7/2019 | Bouserhal | H04R 1/1083 |
| 2020/0134261 A1* | 4/2020 | Cook | G06F 40/289 |

* cited by examiner

DEVICE AND METHOD FOR IMPROVING THE QUALITY OF IN-EAR MICROPHONE SIGNALS IN NOISY ENVIRONMENTS

CROSS-REFERENCE TO RELATED APPLICATIONS

This application claims the benefits of U.S. provisional patent applications Nos. 62/332,861 and 62/460,682, filed on May 6, 2016, and Feb. 2, 2017, respectively, which are herein incorporated by reference.

TECHNICAL FIELD

The present disclosure relates to a device and method for Improving the quality of in-ear microphone signals such as speech and biosignals including breath, heartbeat, etc. in noisy environments. More specifically, the present disclosure relates to an intra-aural device and method for improving the quality of in-ear microphone signals via adaptive filtering and bandwidth extension.

BACKGROUND

Traditionally, communication headsets use a boom microphone, placed in front of the mouth, to capture speech in noisy settings. Although directional, these microphones often suffer from a low signal-to-noise ratio (SNR) in excessively noisy environments and require noise cancellation for enhancement [1]. Alternatively, speech captured through bone and tissue vibrations has been used to provide a signal with a higher SNR [2]. Bone conduction speech can be captured either by microphones placed inside an occluded ear [3] [4] or through bone conduction sensors placed somewhere on the cranium [5]. Although speech generated from bone and tissue conduction can have a relatively high SNR, it suffers from a limited frequency bandwidth (less than 2 kHz), thus reducing signal quality and intelligibility [6]. For applications in which quality and intelligibility are important (e.g. command and control), bone and tissue conduction speech can be a limiting factor. Therefore, to this day, communicating in noise is a difficult task to achieve as the communication signal either suffers from noise interference, in case of airborne speech, or from limited bandwidth, in case of bone and tissue conducted (BTC) speech.

Moreover, in excessively noisy industrial environments where workers are exposed to high level of noise—typically greater than 90 dB(A) for 8 hours—, the Occupational Safety and Health Administration enforces the use of Hearing Protection Devices (HPD) [7]. When worn correctly, HPDs can be very effective in preventing noise induced hearing loss [8], However, limited communication remains the number one complaint of workers equipped with HPDs [9].

Communication headsets are a great way of combining good hearing protection and communication features. Most commonly, headsets made up of circumaural HPDs equipped with a directional boom microphone placed in front of the mouth are used. Circumaurel HPDs can generally provide better attenuation than intra-aural HPDs, because they are easier to wear properly [8]. The disadvantages of these types of communication headsets is two-fold. First, the boom microphone is exposed to the background noise and can still capture unwanted noise, air conducted, that can mask the speech signal of the wearer. Second, circumaural HPDs with boom microphones are not compatible with most other personal protection equipment. The use of other personal protection equipment alongside HPDs Is common in noisy environments. For example, the use of helmets is required for construction workers as are gas masks for fire-fighters. Using bone and tissue conduction microphones to capture speech is a convenient way to eliminate both of those problems, Bone conduction sensors can be placed in various locations and can provide a relatively high SNR speech signal [10]. As mentioned previously, however, the elevated SNR comes at a price of very limited frequency bandwidth of the picked-up signal, typically less than 2 kHz [11]. As a consequence, the enhancement of bone and tissue conducted speech is a topic of great Interest. Many different techniques have been developed for the bandwidth extension of BTC speech [6] [12] [13] [14]. Even though these techniques can enhance the quality of bone and tissue conducted speech, they are either computationally complex or require a substantial amount of training from the user [11], thus limiting their widespread use in practical settings.

An effective compromise between the two extremes of noisy air conducted speech and bandlimited BTC speech captured by bone conduction sensors is speech captured from inside an occluded ear using an in-ear microphone. Occluding the ear canal with an HPD, or more generally an intra-aural device, causes bone and tissue conducted vibrations originating from the cranium to resonate inside the ear canal leading the wearer to hear an amplified version of their voice, this is called the occlusion effect [15]. By way of this occlusion effect, as a consequence of wearing an intra-aural device, a speech signal is available inside the ear and can be captured using an in-ear microphone. Therefore, occluding the ear canal with a highly isolating intra-aural device equipped with an in-ear microphone allows for the capturing of a speech signal that is not greatly affected by the background noise because of the passive attenuation of the intra-aural device. Another advantage of using an in-ear microphone instead of a bone conduction microphone is that the speech is still captured acoustically and can share a significant amount of information with clean speech, such as the one captured—in silence—in front of the mouth in the 0 to 2 kHz range [16]. A bandwidth extension technique that utilizes non-linear characteristics should extend the bandwidth of the in-ear microphone signal and add the high frequency harmonics [17].

However, in extremely noisy situations, some residual noise can exist inside the occluded ear canal and capturing speech through air-conduction can result in a reduced SNR. In these noisy conditions extending the bandwidth of the bandlimited in-ear microphone speech becomes a difficult task because depending on the spectrum of the noise, simple bandwidth extension techniques may actually amplify the noise in the signal and decrease the SNR. Bandwidth extension techniques for noisy speech are rare and are typically computationally complex [12] [18]. Since the SNR of the in-ear microphone speech is relatively high, denoising the speech signal becomes an easier task if the noise information inside the ear canal is known. In such extremely noisy conditions that the in-ear microphone signal becomes noisy, speech captured through air-conduction outside the ear has a very low SNR and is almost completely masked by the noise.

Accordingly, there is a need for a system and method for removing the residual noise extending the frequency bandwidth of signals captured by an in-ear microphone in noisy environments.

SUMMARY

It is therefore a general object of the present disclosure to provide a device and method for removing the residual noise and extending the bandwidth of the signals, such as speech, and biosignals, including breath, heartbeat, etc., captured with an in-ear microphones, for example in an intra-aural device, in noisy environments.

According to an aspect of the present disclosure there is provided a device and method for enhancing speech generated from bone and tissue conduction captured using an in-ear microphone using adaptive filtering and a non-linear bandwidth extension process.

According to an aspect of the present disclosure there is provided a method for detecting speech of a user of an intra-aural device in a noisy environment, the intra-aural device having an in-ear microphone adapted to be in fluid communication with the ear canal of the user and an external microphone, dubbed outer-ear mic, adapted to be in fluid communication with the environment outside the ear, the method comprising the steps of:

acquiring a signal provided by the outer-ear microphone;
applying an adaptive filter on the in-ear microphone signal, using the outer-ear microphone signal as a reference for the ambient noise; the adaptive filter being initialized by an estimated transfer function of the intra-aural device between the outer-ear microphone signal and the In-ear microphone signal; the adaptive filter being represented as a vector of filter weights over a series of time indexes;
upon the computation of an increase in the filter weights of two consequent time indexes greater than a triggering threshold, detecting speech produced by the user.

According to another aspect of the present disclosure there Is provided a method for enhancing speech generated from bone and tissue conduction of a user of an in-ear device in a noisy environment, the intra-aural device having an in-ear microphone adapted to be in fluid communication with the ear canal of the user and an outer-ear microphone adapted to be in fluid communication with the environment outside the ear, the method comprising the steps of:

executing the method for detecting speech produced by the user of an intra-aural device in a noisy environment;
interrupting the application of the adaptive filter to the in-ear microphone signal upon detecting speech by the user;
providing the filtered and denoised signal.

According to a further aspect of the present disclosure there is provided a method as described above, further comprising the step of:

extending the bandwidth of the filtered and denoised signal in the high frequencies using a non-linear bandwidth extension process previous to providing the filtered signal to an interlocutor.

There is also provided a device for enhancing speech generated from bone and tissue conduction of a user of an intra-aural device in a noisy environment, the device comprising:

an intra-aural device adapted to be located into the ear canal of the user, the intra-aural device having an in-ear microphone adapted to be in fluid communication with the ear canal of the user and an outer ear microphone adapted to be in fluid communication with the environment outside the ear; and
a processing unit operatively connected to the in-ear microphone to receive an internal signal therefrom, to the outer-ear microphone to receive an external signal therefrom and to send a resulting signal to an interlocutor, the processing unit being configured so as to:
execute the method for enhancing speech generated from bone and tissue conduction of a user of an intra-aural device in a noisy environment.

There is also provided a device and method for picking-up, with the in-ear microphone of an intra-aural device occluding the ear canal of the user, the physiological noises that are present in the occluded ear canal and to further filter and denoise these biosignals for monitoring applications.

Other objects and advantages of the present disclosure will become apparent from a careful reading of the detailed description provided herein, with appropriate reference to the accompanying drawings.

BRIEF DESCRIPTION OF THE DRAWINGS

Embodiments of the disclosure will be described by way of examples only with reference to the accompanying Figures, in which.

DETAILED DESCRIPTION

Generally stated, the non-limitative illustrative embodiments of the present disclosure provide a device and method for improving the quality of in-ear microphone signals, such as speech, and biosignals, including breath, heartbeat, etc., in noisy environments. It is to be understood that although the present disclosure relates mainly to a device and method for Improving the quality of in-ear microphone speech signals, the technique disclosed can improve the quality of any of the aforementioned signals via adaptive filtering and bandwidth extension.

Bone and tissue conducted speech has been used to provide a relatively high Signal-to-Noise Ratio (SNR) in noisy environments. However, the limited bandwidth of bone and tissue conducted speech degrades the quality of the speech signal. In very noisy conditions, bandwidth of the bone and tissue conducted speech becomes problematic. The disclosed device and method use an adaptive filtering approach to denoise the bone and tissue conducted speech signal and, once the signal is denoised, extended its bandwidth by creating odd harmonics in order to recreate the high frequency harmonics.

More specifically, this is performed, in real time, using an in-ear and an outer-ear microphones, the in-ear microphone picks up speech generated from bone and tissue conduction and generates a speech signal to which an adaptive filter is applied in order to denoise using the signal from the outer-ear microphone. A voice activity detection criteria using the filter coefficients of the adaptive filter is used to ensure that only noise is reduced while the speech content of the speech signal from the in-ear microphone remains unaffected. Once the speech signal is denoised, its bandwidth is extended by exploiting the nonlinear characteristics of a cubic operator.

The bandwidth extension of the denoised in-ear microphone speech signal significantly enhances Its quality. For noisy environments, for example a factory, the described method provides a simple, speaker independent, non-computationally exhaustive method to enhance the quality of speech picked up using an in-ear microphone. Overall, gains of 1.23 (out of 4.5) in Perceptual Objective Listening Quality Assessment (POLQA) Objective Listening Quality-Mean Opinion Score (MOS-LQO) scores and 45 (out of 100) in MUltiple Stimuli with Hidden Reference and Anchor (MUSHRA) scores have been observed, which show the benefits of the proposed speech enhancement solution.

Figure 1:
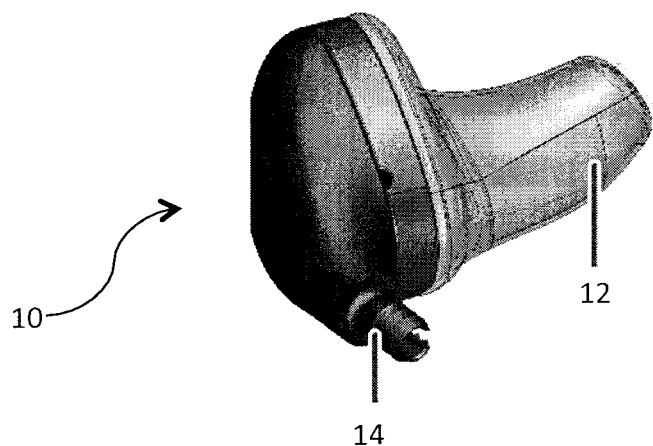
FIG. 1 is a perspective view of an intra-aural device for improving the quality of in-ear microphone signals in noisy environments in accordance with an illustrative embodiment of the present disclosure.
Figure 2:
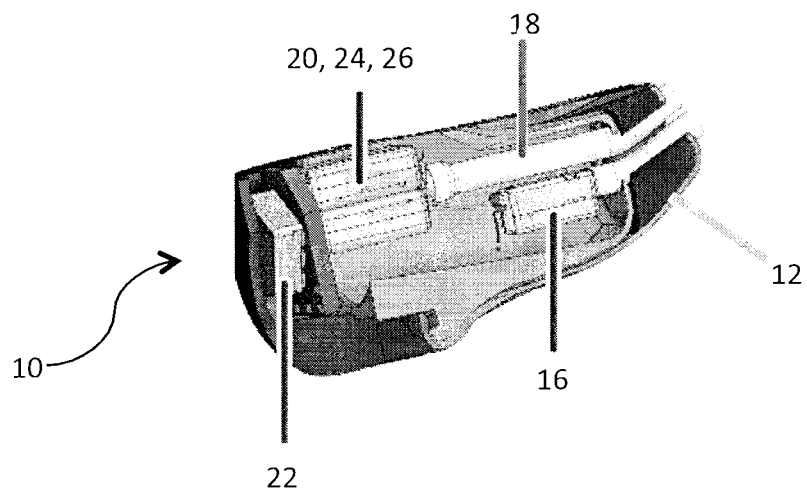
FIG. 2 is a cross-section of the intra-aural device of FIG. 1.
Figure 3:
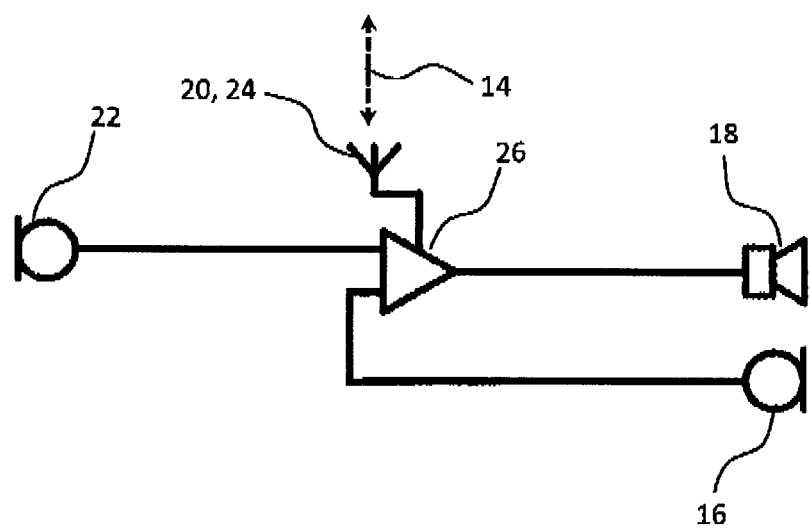
FIG. 3 is a schematic architecture diagram representation of the intra-aural device of FIG. 1.

Referring to FIG. 1, the intra-aural device for improving the quality of in-ear microphone signals in noisy environments 10, in accordance with an illustrative embodiment of the present disclosure, takes the form of an intra-aural unit 12 generally conforming to the ear canal of a user, which may be inflatable, compressible, custom molded, etc., for passive attenuation of ambient noise and a communication link 14, for example a wireless or Bluetooth communication link. Referring now to FIGS. 2 and 3, the intra-aural device 10 generally includes an in-ear microphone (IEM) 16, a miniature loudspeaker 18, a receiver 20, an outer-ear microphone (OEM) 22 located flush on the outer face of the intra-aural unit 12, transmitter 24, all of which, along with the wireless communication link 14, are operatively connected to a digital signal processing (DSP) unit 26 having an associated memory comprising instructions stored thereon that, when executed on the processor of the DSP unit 26, perform the steps of the various processes which will be further described below. It is to be understood that in alternative embodiments some or all of the receiver 20, transmitter 24 and DSP 26 may be located outside the intra-aural unit 12, for example in an external unit worn by the user of the Intra-aural device 10.

Figure 4A:
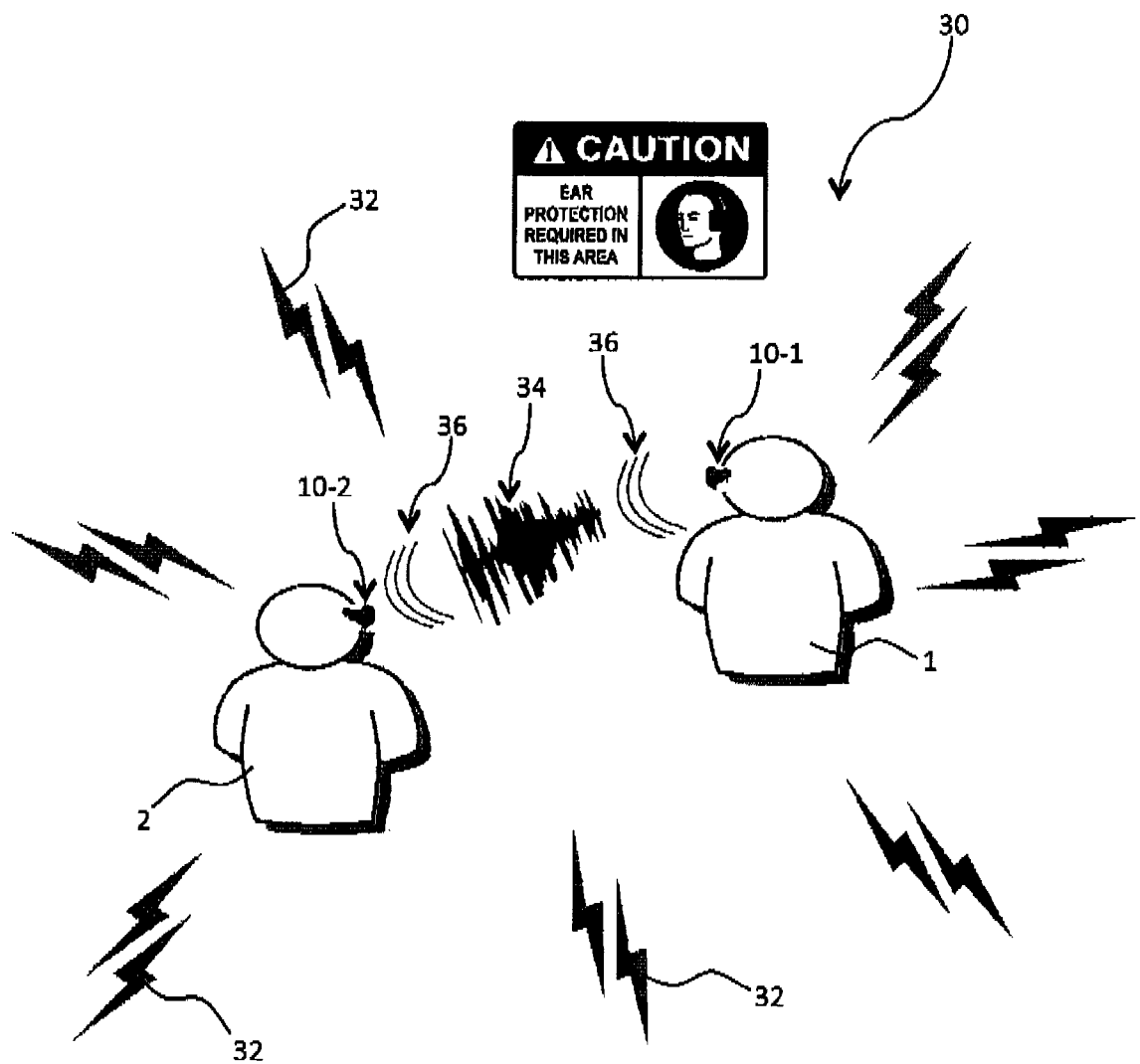
FIG. 4A is a schematic representation of two users communicating (only one way presented) in a noisy environment using intra-aural the device of FIG. 1.
Figure 4B:
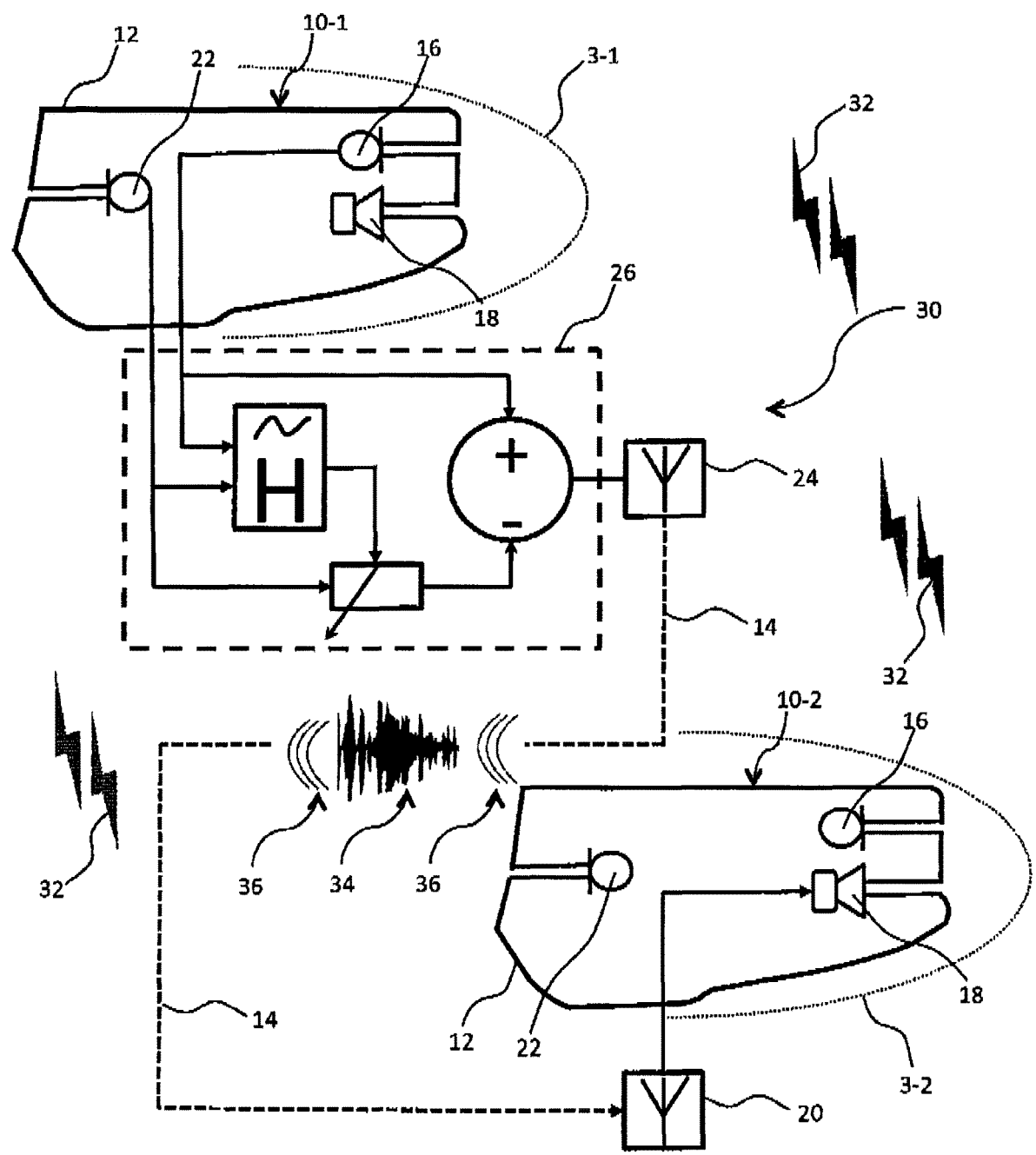
FIG. 4B is a block diagram representing the interconnections between in-ear microphones, outer-ear microphones and internal speakers of the intra-aural device used by the two users communicating in FIG. 4A.

Referring to FIGS. 4A and 4B, there is shown two users 1, 2 wearing infra-aural devices 10-1 and 10-2, respectively, communicating in a noisy environment 30 having a variety of noise sources 32. In the illustrated scenario, user 1 is the speaker and user 2 the listener. When user 1 speaks, the IEM 16 of device 10-1 picks up speech generated from bone and tissue conduction of user 1 and generates a speech signal to which, using the DSP unit 26, the adaptive filter is applied in order to denoise the speech signal using the signal from the OEM 22. The voice activity detection criteria, which uses the filter coefficients of the adaptive filter, ensures that only the noise 32 is reduced while the speech content of the speech signal from the IEM 16 remains unaffected. Once the speech signal is denoised, its bandwidth is extended by exploiting the nonlinear characteristics of a cubic operator. The resulting improved speech signal 34 is then transmitted 38, using the transmitter 24, from device 10-1 to device 10-2 via wireless communication link 14, which provides, when received by receiver 20, the improved speech signal 34 to the loudspeaker 18 of intra-aural device 10-2 and hence user 2. It is to be noted that all of the described steps are performed in real time.

is to be understood that in an alternative embodiment the improved speech signal 34 maybe transmitted to another device, for example a smart phone or other such device.

The presence of the OEM 22 and IEM 16 allows the determination of the relationship between the sound outside the ear and inside the ear, i.e. the transfer function of the intra-aural device 10. This provides insight about the "in-ear" noise and enables denoising through adaptive filtering. Once the IEM 16 speech signal is denoised, bandwidth extension can then be performed to further improve quality.

Intra-Aural Device Transfer Function Identification

The Intra-aural device 10 transfer function is estimated, as it varies from user to user. This is accomplished by exposing a worn device for improving the quality of in-ear microphone speech in noisy environments 10 to white noise at 85 dB (SPL) using a loudspeaker outside the ear for at least 2 seconds. The OEM 22 and IEM 16 simultaneously capture the signals outside and inside the ear respectively and the transfer function of the intra-aural device 12, H(z), estimated as $\hat{H}(z)$.

In-Ear Microphone Noise Reduction

Once the noise level is high enough that the OEM 22 speech signal is almost completely masked (i.e. SNR<−5 dB), the IEM 16 speech signal can be denoised using normalized least mean squared (NLMS) adaptive filtering. The choice of adaptive filtering comes from a need to create an algorithm that assumes no properties about the noise and is, thus, robust to various types of noise. Therefore, using adaptive filtering is beneficial for the user by enhancing the received communication signal.

Figure 5A:
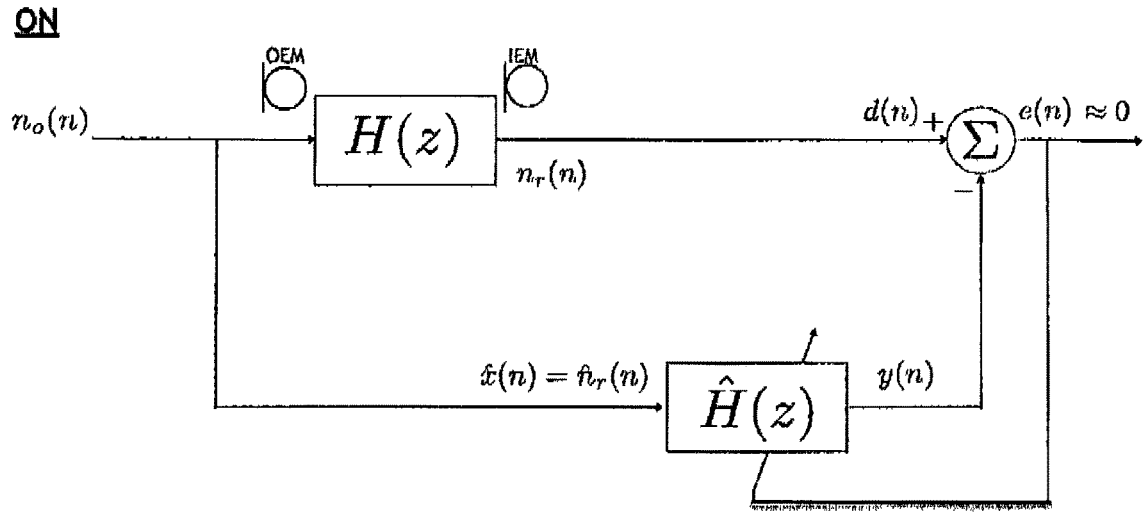
FIGS. 5A and 5B are block diagrams representing the normalized least mean squared (NLMS) adaptive filtering stage when the adaptation is ON (FIG. 5A) and when it is OFF (FIG. 5B)
Figure 5B:
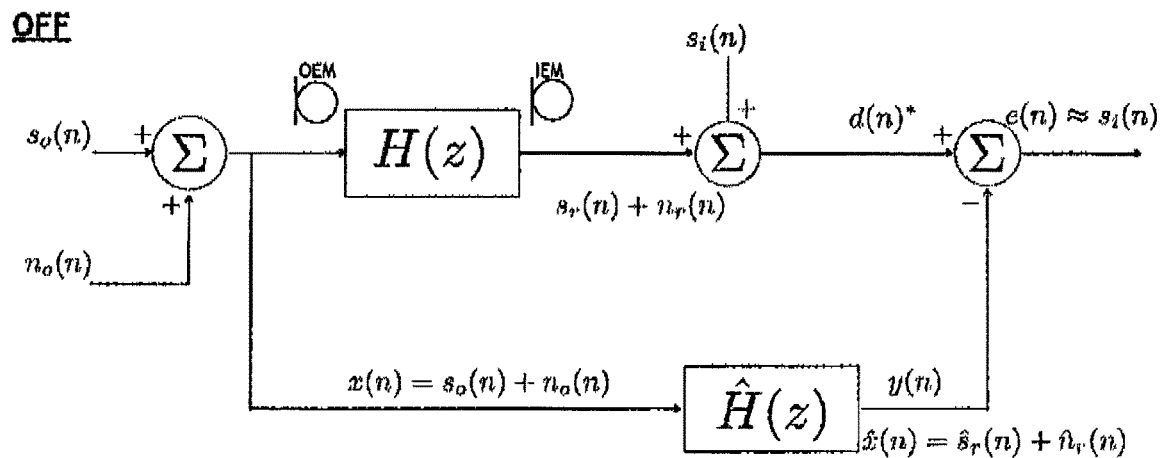

To properly denoise the IEM 16 speech signal produced by the user without affecting the speech content, the adaptation process must be frozen (OFF) when the user is speaking and active (ON) when the user is not speaking. This ensures that the adaptive filter cancels only the noise and does not interfere with any speech produced by the user. The two states of the adaptive filter are shown in FIGS. 5A and 5B. When the adaptation is ON (FIG. 5A) the structure of the proposed adaptive filter follows the well-known structure commonly described in the literature [19]; the only exception being that the signal of interest is the error signal, e(n). Here, H(z) is the true transfer function of the intra-aural device 12 while $\hat{H}(z)$ is the estimated intra-aural device 12 transfer function. When the adaptation is ON (FIG. 5A), the user is not speaking. The OEM 22 captures the noise outside the ear, $n_o(n)$, while the IEM 16 captures the residual noise inside the ear $n_r(n)$, colored by H(z). The signal captured by the IEM 16 is defined as the desired signal, d(n). The input, x(n), to the adaptive filter is the signal captured by the OEM 22 filtered with the adaptive filter which is initialized by the estimated transfer function of the intra-aural device 12 $\hat{H}(z)$. The output of the adaptive filter, y(n), is thus a close estimate of the residual noise inside the ear and the difference between d(n) and y(n) should approach 0. The adaptive filter of order 180 is defined as follows:

$$y(n) = w^T(n-1)x(n),$$

$$e(n) = d(n) - y(n),$$

$$w(n) = w(n-1) + \frac{\mu e(n)x(n)}{\epsilon + x(n)^T x(n)},$$

where n is the current time index, µ is the adaptation step size, w(n) is the vector of filter weights at time index n, and $\in$ is a very small number to avoid division by zero.

When the adaptation is OFF (FIG. 5B), let $s_o(n)$ and $n_o(n)$ be the speech signal produced by the user and noise signal outside the ear, respectively. Therefore, the OEM 22 picks up the sum of these two signals, x(n). Meanwhile, the IEM 16 picks up the residual noise signal after the attenuation of the intra-aural device 12, $n_r(n)$, and the residual speech signal $s_r(n)$. The speech signal originating from bone and tissue conduction, $s_t(n)$, is also picked up by the IEM 16. The sum of all three signals picked up by the IEM 16 is the desired signal d(n). The signal x(n) picked up by the OEM 22 is then filtered using the $\hat{H}(z)$ and the output, $\hat{x}(n)$, is fed to the input of the NLMS adaptive filter. The output of the adaptive filter, y(n) is then subtracted from d(n). The adaptive filter brings the difference between the residual noise, $n_r(n)$, and the estimated residual noise, $\hat{n}_r(n)$ to zero. Since the OEM 22 speech signal is almost entirely masked by the noise, the effect of s (n) and $\hat{s}_r(n)$ is negligible. Therefore, the resulting difference between the output of the adaptive filter and the signal captured by the IEM 16 is the speech signal originating from bone and tissue conduction, $s_t(n)$, with minimal effects of noise.

Adaptation Process

Figure 6:
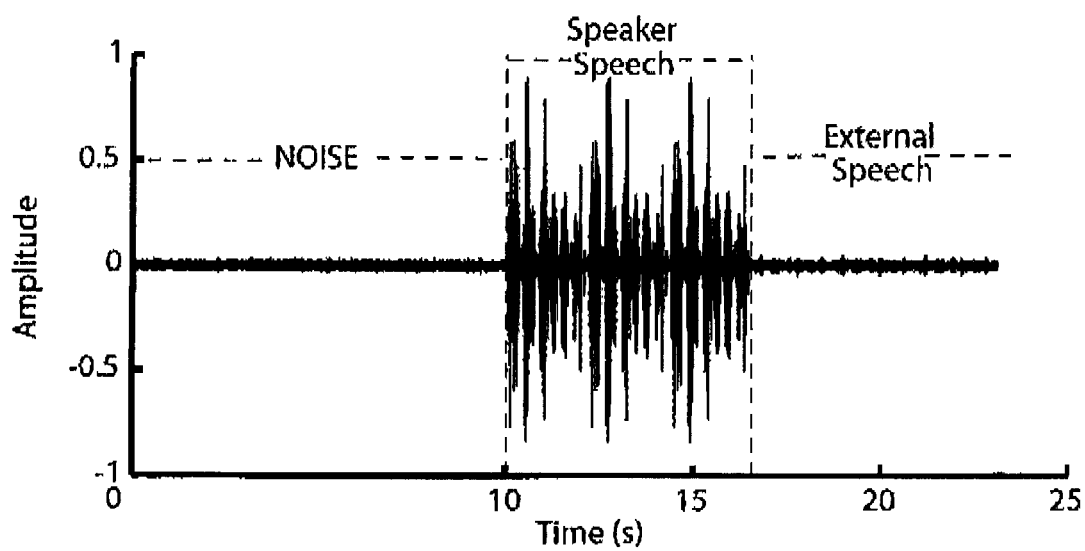
FIG. 6 is a schematic plot diagram of an example of a test signal for the in-ear microphone (IEM) to optimize speech detection criteria.

To achieve denoising without affecting the speech content, the adaptation process is a function of whether or not the user is speaking. To denoise the user's speech, the adaptive filter must only adapt when the user is not speaking. This ensures that the filter is adapting to the intra-aural device 12 transfer function (i.e. H(z)) and thus the noise and only the noise is subtracted from the signal and not any relevant speech information. To guarantee robustness of the speech detection process, voice activity detection inside the ear is achieved by monitoring the value of the coefficients of the adaptive filter. After completion of the two second identification stages, the vector of filter weights over the entire index of time, w, is used to detect if the user is speaking. To decide what criteria can be used to detect speech inside the ear using filter weights, test signals can be used, for example the first 10 lists of the recorded Harvard phonetically balanced sentences, for both the OEM 22 and the IEM 16, each test signal starting with at least 2 seconds of noise followed by 8 to 10 seconds of speech either by the user or by an external competing speaker. Exterior speech can be added to simulate a case where the user is not speaking but loud enough that some residual speech exists after the passive attenuation of the intra-aural device 12, The residual speech should not trigger the speech activity of the adaptation process. For the IEM 16 signal, the residual speech can be simulated by passing the speech through $\hat{H}(z)$. The location of the user's speech and the residual speech is randomized to avoid any trends in the adaptation process. FIG. 6 shown an example of a randomly chosen IEM 16 test signal with both user speech and external speech segments.

Through analysis of the changes in the filter weights for the test signals, it was concluded that the maximum valued filter weight can be chosen as a good triggering criteria. Once the maximum filter weight increases more than a triggering threshold, $T_g$, from one time index to the other, it is predicted that the user is speaking. Therefore once $$\frac{\max(w(n))}{\max(w(n-1))} \geq T_g,$$

speech by the user is detected and the adaptation is turned OFF (FIG. 5B).

$T_g$ Value Selection

The value for $T_g$ has to be selected such that it is not particular to a specific speaker. This can per performed using recorded conversations, through the IEM 16 and the OEM 22, from different speakers (varying gender, age, etc.), for which is analyzed the effect of using different triggering thresholds. A sweep of the voice activity detection triggering threshold, $T_g$, is then performed, for example a sweep from $T_g=1.01$ to $T_g=1.20$ with a step size of 0.01, during the adaptation process. The bandwidth of the denoised signals for the various speakers resulting from the sweep is extended using a bandwidth extension (BWE) process, which will be further detailed below. The quality of those signals is measured before and after the BWE to see the effect of the different values for the triggering criteria. The choice of $T_g$ is then made as the triggering percentage value that produces the optimal objective quality over the various speakers. In the illustrative example, a peek was observed at around $T_g=1.06$-1.07, suggesting a triggering threshold of $T_g=1.06$ to detect speech activity inside the ear.

The change in filter weights is triggered at the onset of speech but not the end. To ensure that the adaptive process starts back once speech inside the ear is no longer present the overall change in energy, $\Delta_\in$, at the onset of speech Is also measured and monitored, per sample, i.e. $\Delta_\in(n)$. Once triggered by the user's speech, the adaptation is disabled for at least one second and as long as $\Delta_\in$ is maintained. When the adaptation is OFF the filter weights of the adaptive filter are updated with those from the previous second, w(n−fs). This is to ensure that the filter weights are those from when no speech is produced by the user. Once the change in energy is less than the onset change, $\Delta_\in(n)<\Delta_\in$, the adaptation starts again. The process of monitoring the change in $\Delta_\in$ gives a non-ad-hoc way to turn ON the adaptation once the user is no longer speaking.

Figure 7:
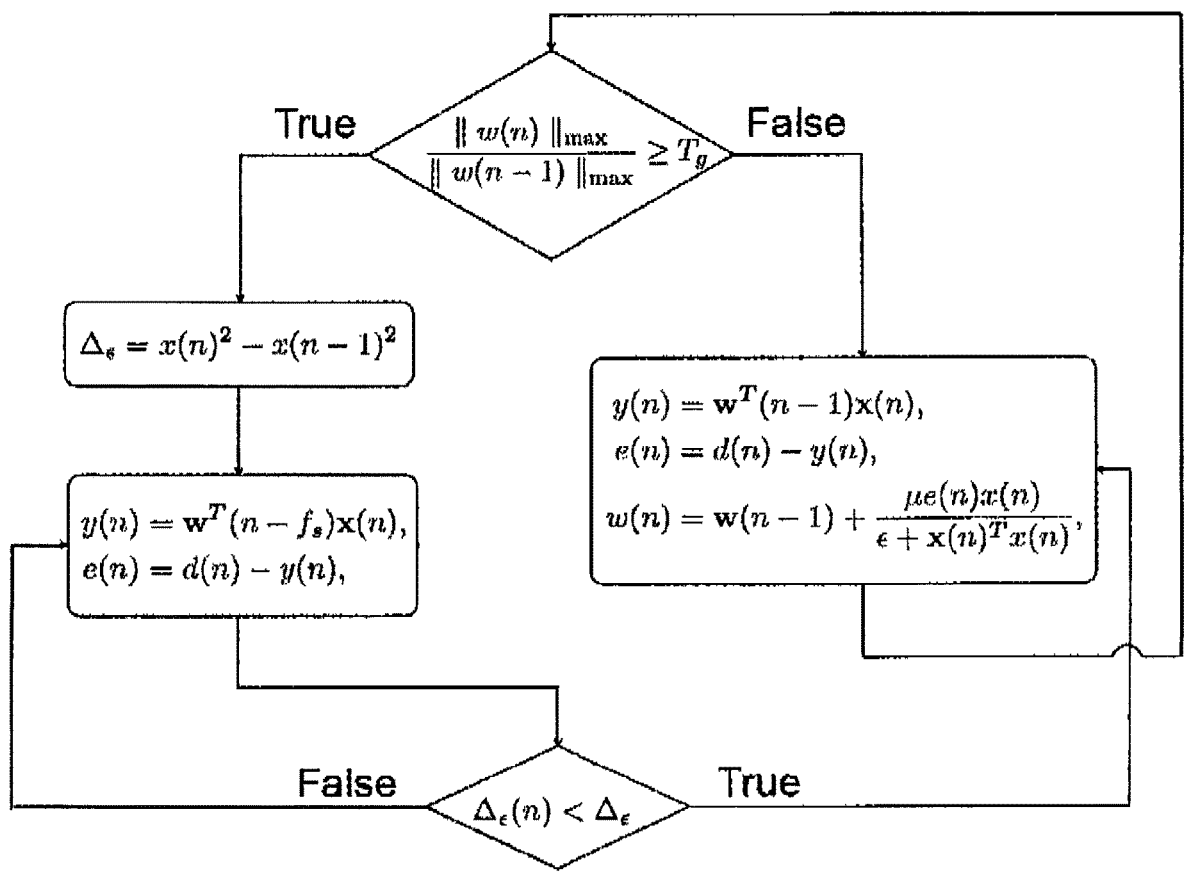
FIG. 7 is a flow diagram of the adaptation process for the adaptive filter use to denoise the in-ear microphone (IEM) signals.

The adaptation process is illustrated by the flow diagram in FIG. 7.

The adaptive filtering denoises the IEM 16 signal by utilizing the information about the noise captured by the OEM 22. Once the IEM 16 is denoised its quality can be enhanced by extending its bandwidth in the high frequencies using the BWE.

It is to be understood that the triggering threshold, $T_g$, can be set a priori at the time of manufacturing or, in an alternative embodiment, may be set using a calibration process such that $T_g$ is specific to the user and/or the intra-aural device 12.

Bandwidth Extension Process

Figure 8:
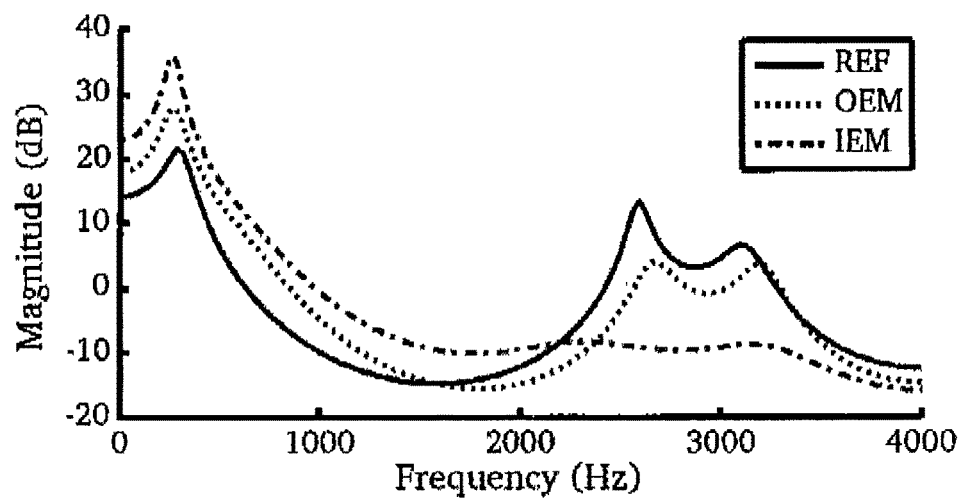
FIG. 8 is a schematic plot diagram of an example of the linear predictive coding (LPC) spectral envelope of the phoneme/l/recorded with the reference microphone (REF), the outer-ear microphone (OEM) and the in-oar microphone (IEM) simultaneously.
Figure 9:
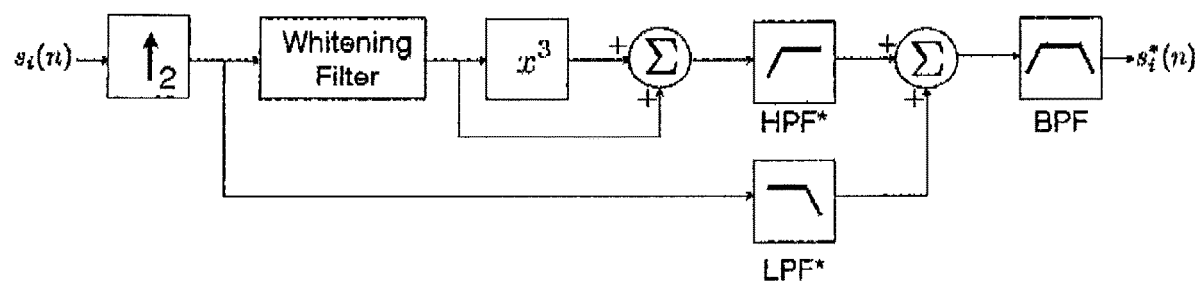
FIG. 9 is a block diagram of the bandwidth extension process.

Artificially extending the bandwidth of a clean bandlimited signal has been very well studied, With reference to FIG. 8, since the IEM 16 signal shares mutual information with the reference speech signal, i.e. picked up using a reference microphone (REF) placed in front of the mouth, between 0-2 kHz [16], it is only necessary to extend the bandwidth in the high frequency range, 2-4 kHz. As described by [17], a simple yet effective way of extending the bandwidth is through the application of the signal's nonlinear characteristics. FIG. 9 shows a block diagram of the bandwidth extension process. First, the signal is upsampled by a factor of 2 to provoke spectral folding. To reach an excitation signal similar to that extracted from a wideband speech signal, the upsampled signal is filtered by a whitening filter using the coefficients of a linear predictive coding (LPC) analysis [20]. The whitening filter is a finite infinite response filter whose coefficients are those of an 18th order LPC filter at that time frame. Cubing the excitation reproduces the odd harmonics along the entire bandwidth including the high band, in this scenario from 1.8 kHz to 4 kHz. Since the high frequencies are the only region of interest and to eliminate any overlap, the excitation signal is high passed at 1.8 kHz with a third order filter. Meanwhile, the upsampled IEM 16 signal is low passed at 1.8 kHz with a third order filter because it contains no relevant frequency information above 1.8 kHz (see FIG. 8). The high pass filter used for the excitation signal and the low pass filter used for the upsampled IEM 16 signal are designed to be power complementary for perfect reconstruction. The sum of the two filtered signals is then band passed with a fourth order Linkwitz-Riley filter at 160 Hz and 3.5 kHz by cascading a second order low pass Butterworth filter and a second order high pass Butterworth filter. This is done to eliminate the boomy effect coming from the bone and tissue conduction as well as any ringing caused by the odd harmonics of the cubed excitation signal. The overall output is then downsampled by a factor of 2 to go back to an 8 kHz sampling frequency. It is important to note that this bandwidth extension technique adds missing harmonics in the high frequencies. However, missing formants and friction noise are not recovered.

Although the adaptation process was described in the context of denoising a user's speech signal, the determination of whether or not the user is speaking may also be used in an alternative embodiment in order to Interrupt another process when the user is speaking, for example the recording of some biological process (i.e. heart rate, respiration, etc.). In a further alternative embodiment, the adaptation process may be adapted to detect sounds inside a device or space enclosed in a noisy environment, i.e. the in-ear microphone takes the form of an in-device/space microphone and the outer-ear microphone takes the form of an outer-device/space microphone.

Figure 10A:
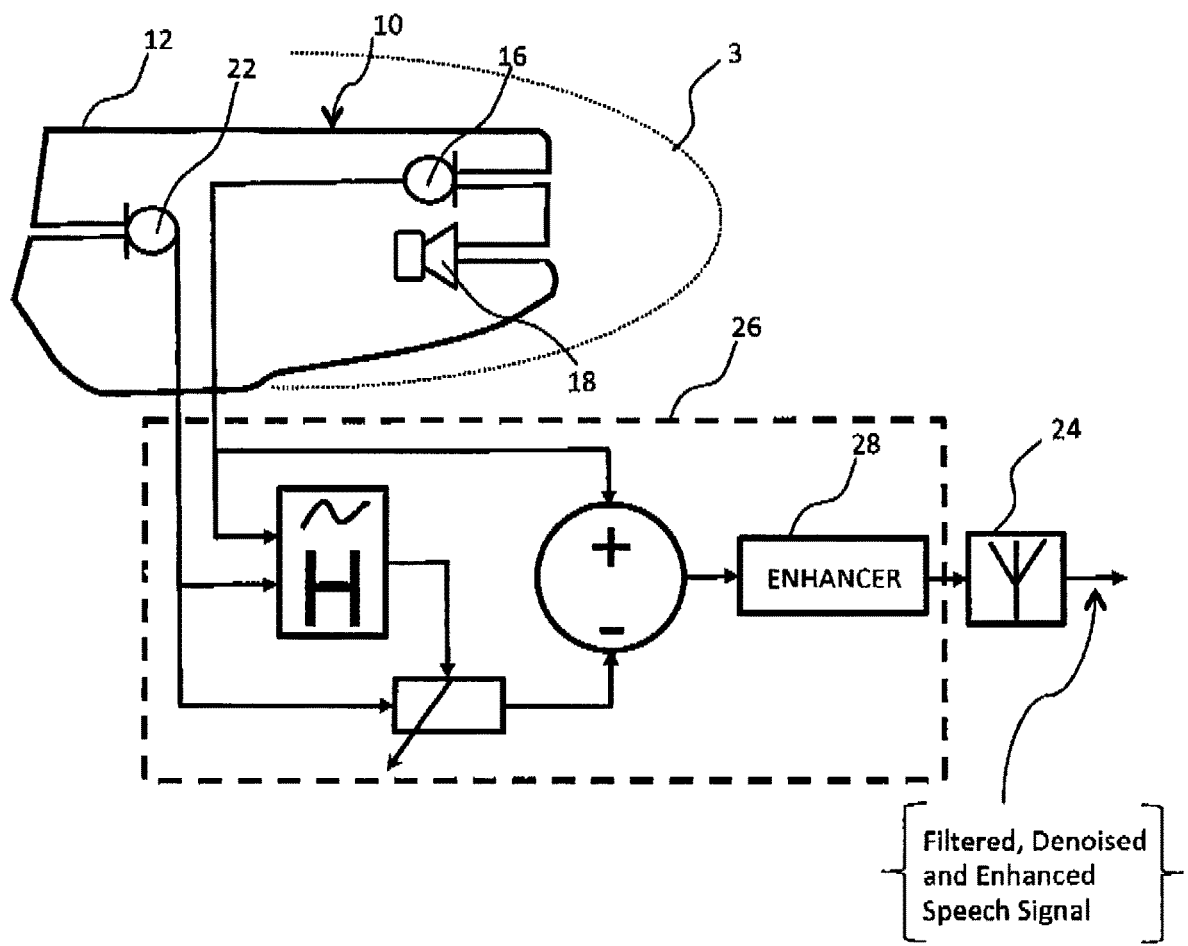
FIGS. 10A, 10B and 10C are block diagrams of the various input-outputs of the intra-aural device of FIG. 1, including the filtered, denoised and enhanced in-ear speech signal (FIG. 10A), the filtered and denoised biosignals (FIG. 10B) and the Voice Activity Detector (VAD) output state (FIG. 10C)
Figure 10B:
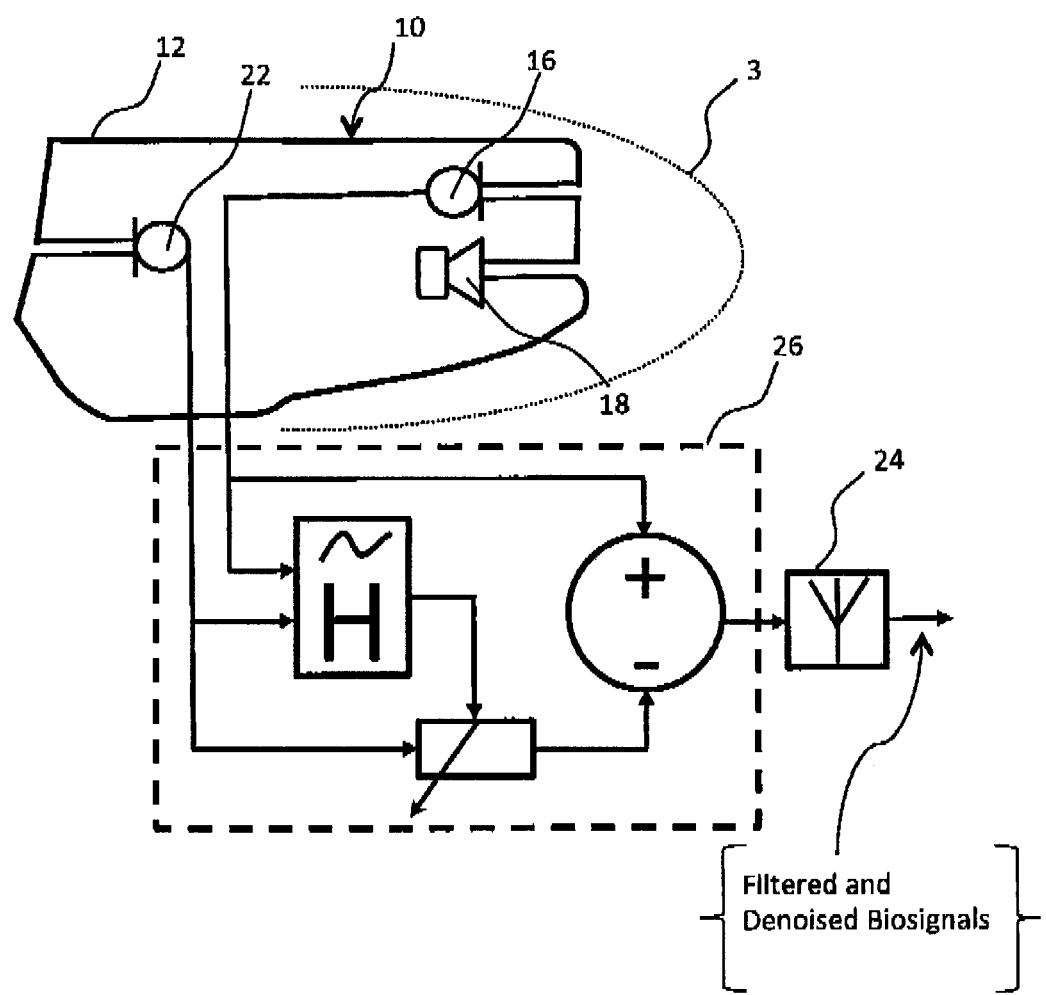
Figure 10C:
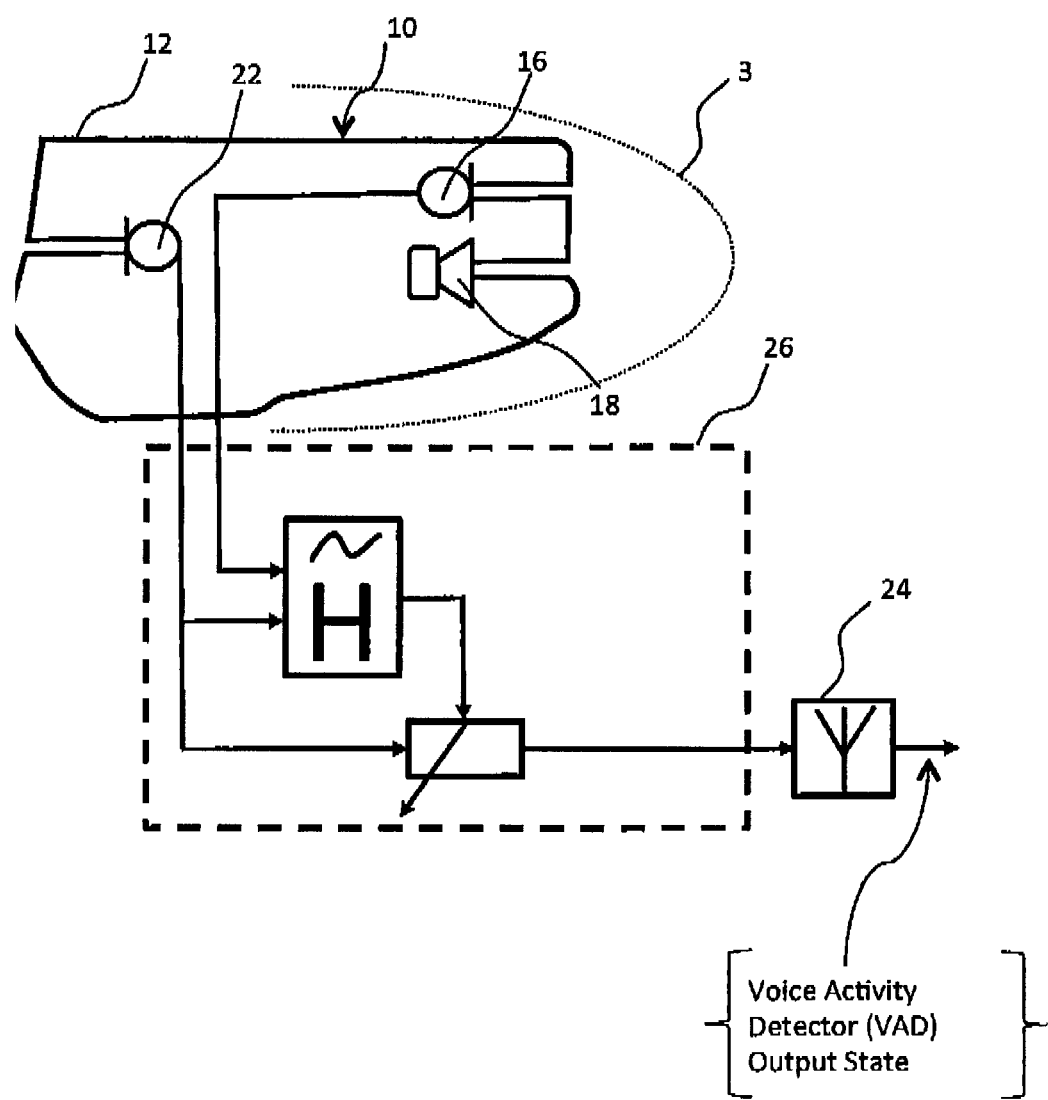

Referring to FIGS. 10A to 10C, there are shown various alternative use of the intra-aural device 10, which include the providing of a filtered, denoised and enhanced (using enhancer 28) in-ear speech signal (FIG. 10A), filtered and denoised biosignals (FIG. 10E) and a Voice Activity Detector (VAD) output state, i.e. a signal indicating the presence or not of voice activity of the user, which can be used for automatic activation of a personal communication system, such as voice activation, voice operated switch or Voice Operated Exchange (VOX) in a two-way radiocommunication device (FIG. 10C).

Figure 11:
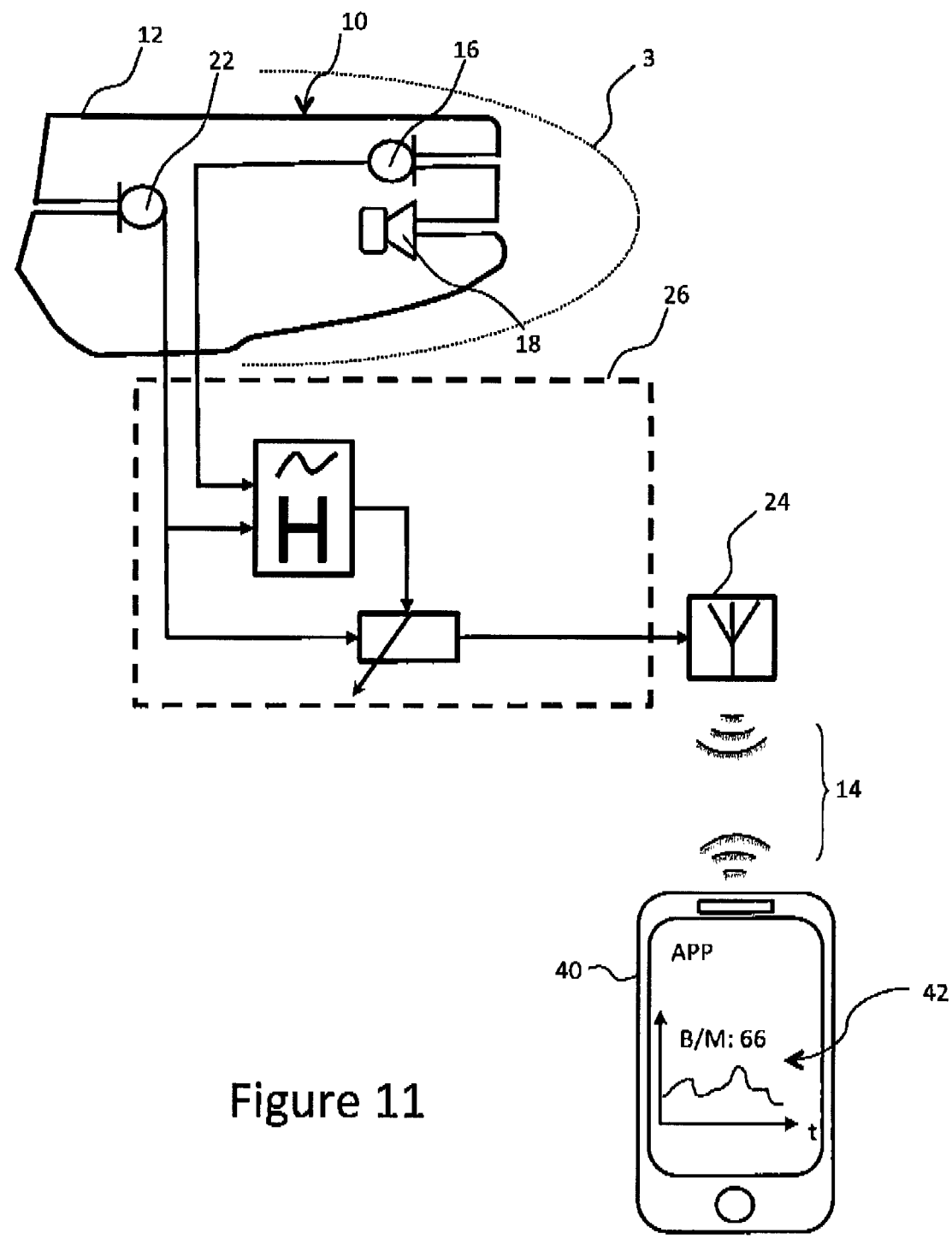
FIG. 11 is a schematic representation of an example of use of the intra-aural device of FIG. 1 as a portable application for biosignal monitoring.

Referring now to FIG. 11, there is shown an example of use of the intra-aural device 10 as a portable application for biosignal monitoring. The intra-aural device 10 transmits biosignals of a user via wireless communication link 14, using transmitter 24, to a smart phone 40 on which runs a biosignal monitoring application 42 that can analyze and/or display the biosignals. The application 42 may also warn the user of some specific condition if detected.

Figure 12:
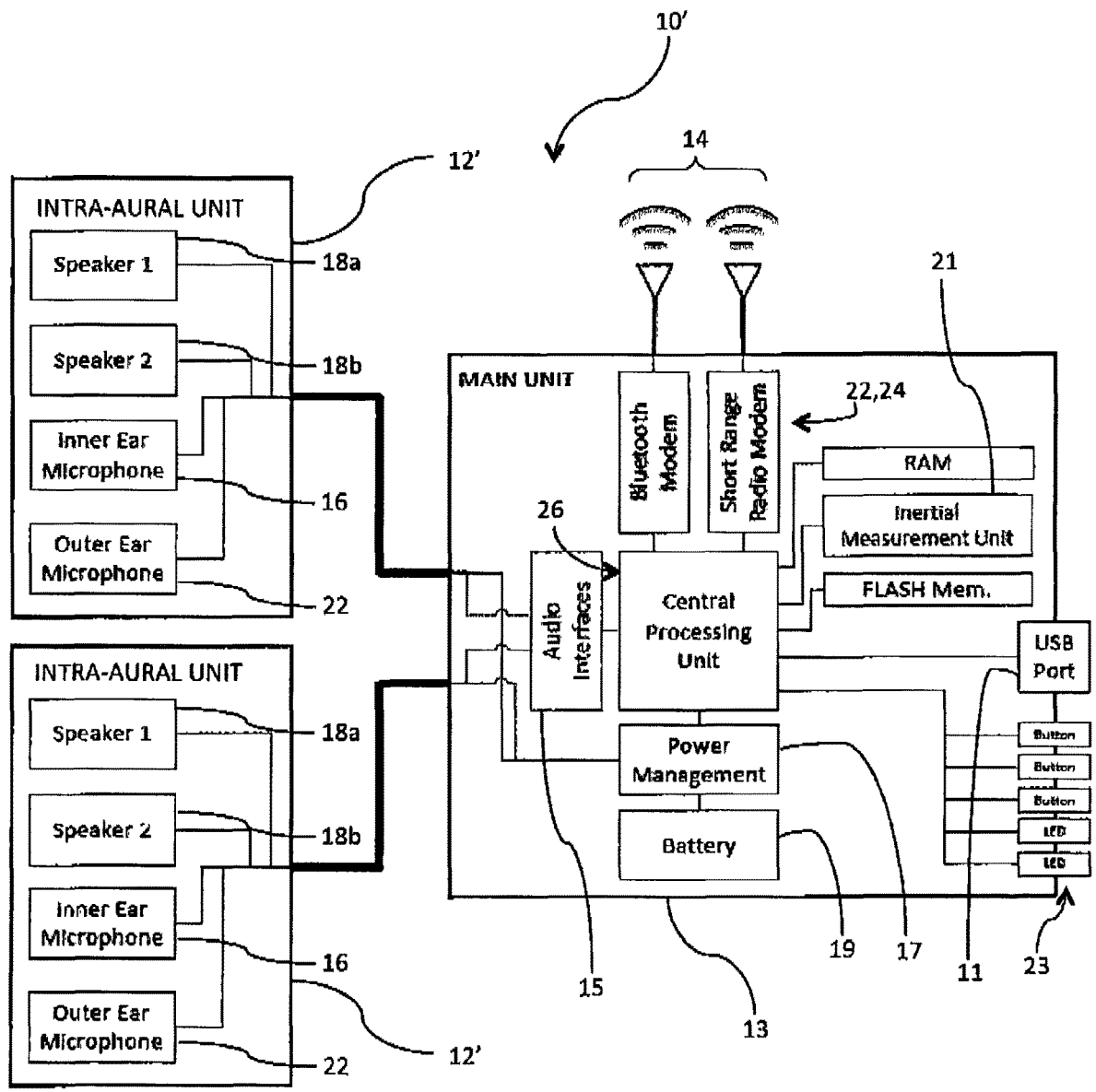
FIG. 12 is a block diagram of an intra-aural system for communicating in noisy environments in accordance with another Illustrative embodiment of the present disclosure.

Referring to FIG. 12, there is shown an intra-aural system for communicating in noisy environments 10' in accordance with another illustrative embodiment of the present disclosure, which takes the form of a pair of intra-aural units 12' and a main unit 13. Each intra-aural unit 12', includes an in-ear microphone 16, an outer-ear microphone 22 and a pair of miniature loudspeakers 18a, 18b. The receiver 20, transmitter 24 and processing unit 26 are externally located inside a main unit 13 operatively connected to each of the intra-aural units 12'. The main unit 13 includes audio interfaces 15 for communication with the intra-aural units 12', a power manager 17 and battery 19 for providing power to the components of the intra-aural 12' and main 13 units, a processing unit 26 in the form of a central processing unit with associated memory (RAM, FLASH memory), a receiver 22 and transmitter 24 in the form of blue tooth and short range radio modems for providing a communication link 14 to remote components, an inertial measurement unit 21, a USB port 11 for accessing the associated memory and configuring the central processing unit 26, and a plurality of buttons and LEDs 23 for providing various functionalities to a user of the intra-aural communication system 10'.

Although the present disclosure has been described with a certain degree of, particularity and by way of illustrative embodiments and examples thereof, it is to be understood that the present disclosure is not limited to the features of the embodiments described and illustrated herein, but includes all variations and modifications within the scope and spirit of the disclosure as hereinafter claimed.

LIST OF REFERENCES

[1] Gan, W. and Kuo, S. "Integrated active noise control communication headsets." Proceedings of International Symposium on Circuits and Systems, 4:IV 353-IV-356 (2003).

[2] Casali, J. and Berger, E. "Technology advancements in hearing protection circa 1995: Active noise reduction, frequency/amplitude-sensitivity, and uniform attenuation." American Industrial Hygiene Association, 57(2): 175-185 (1996).

[3] Bou Serhal, R., Falk, T., and Voix, J. "Integration of a distance sensitive wireless communication protocol to hearing protectors equipped with in-ear microphones," In Proceedings of Meetings on Acoustics, volume 19, 040013. Acoustical Society of America (2013).

[4] Kondo, K., Fujita, T., and Nakagawa, K. "On equalization of bone conducted speech for improved speech quality." Sixth IEEE International Symposium on Signal Processing and Information Technology, ISSPIT, 426-431 (2007).

[5] Zheng, Y., Liu, Z., Zhang, Z., Sinclair, M., Droppo, J., Deng, L., Acero, A., and Huang, X. "Air- and boneconductive integrated microphones for robust speech detection and enhancement," 2003 IEEE Workshop on Automatic Speech Recognition and Understanding (IEEE Cat. No. 03EX721), 3-8 (2003).

[6] Turan, T. and Erzin, E. "Enhancement of throat microphone recordings by learning phone-dependent mappings of speech spectra." In IEEE International Conference on Acoustics, Speech and Signal Processing, 7049-7053. IEEE (2013).

[7] OSHA, U. S. Occupational Noise Exposure: Hearing Conservation Amendment, Final Rule. Federal Register (1983).

[8] Berger, E. The Noise Manual. AIHA (2003).

[9] NIOSH. "Advanced Hearing Protector Study." Technical report, Flint, Mich. (2005).

[10] McBride, M., Tran, P., Letowski, T., and Patrick, R. "The effect of bone conduction microphone locations on speech intelligibility and sound quality." Applied ergonomics, 42(3):495-502 (2011).

[11] Shin, H. S., Kang, H., and Fingscheidt, T. "Survey of speech enhancement supported by a bone conduction microphone." In Speech Communication; 10. ITG Symposium; Proceedings of, 1-4, VDE (2012).

[12] Li, M., Cohen, I., and Mousazadeh, S. "Multisensory speech enhancement in noisy environments using bone-conducted and air-conducted microphones." In Signal and Information Processing (ChinaSIP), 2014 IEEE China Summit & International Conference on, 1-5. IEEE (2014).

[13] Dekens, T. and Verhelst, W. "Body Conducted Speech Enhancement by Equalization and Signal Fusion," (2013).

[14] Rahman, M. and Shimamura, T. "Intelligibility enhancement of bone conducted speech by an analysis-synthesis method." 2011 IEEE 54th International Midwest Symposium on Circuits and Systems (MWSCAS), 1-4 (2011).

[15] Bernier, A. and Voix, J. "An active hearing protection device for musicians." In Proceedings of Meetings on Acoustics, volume 19, 040015. Acoustical Society of America (2013).

[16] Bouserhal, R., Falk, T., and Voix, J. "On the potential for Artificial Bandwidth Extension of Bone and Tissue Conducted Speech: A Mutual Information Study." In International Conference on Acoustics, Speech, and Signal Processing, 2015., volume 1, 665-668. IEEE (2015).

[17] Isar, B. and Schmidt, G. "Bandwidth extension of telephony speech." In Speech and Audio Processing in Adverse Environments, chapter 5, 135-184 (2008),

[18] Seltzer, M., Acero, A., and Droppo, J. "Robust Bandwidth Extension of Noisecorrupted Narrowband Speech." Interspeech 2005, 1509-1512 (2005).

[19] Manolakis, D., Ingle, V., and Kogon, S. "Statistical and adaptive signal processing: spectral estimation, signal modeling, adaptive filtering, and array processing", volume 46. Artech House Norwood (2005).

[20] Valin, J.-M. and Lefebvre, R. "Bandwidth, extension of narrowband speech for low bit-rate wideband coding", in Speech Coding, 2000. Proceedings, 2000 IEEE Workshop on, pages 130-132, IEEE. Delavan, Wis., USA.

We claim:

1. A method for enhancing speech generated from bone and tissue conduction of a user of an intra-aural device in a noisy environment, the intra-aural device having an in-ear microphone adapted to be in fluid communication with an outer ear canal of the user and an outer-ear microphone adapted to be in fluid communication with an environment outside an ear, the method comprising the steps of:

acquiring a signal from the in-ear microphone;
acquiring a signal from the outer-ear microphone;
applying an adaptive filter to the acquired in-ear microphone signal to produce a denoised signal, the adaptive filter:
  being initialized by an estimated transfer function of the intra-aural device based on the outer-ear microphone signal and the in-ear microphone signal;
  having an adaptation process continuously adjusting the estimated transfer function using the acquired in-ear microphone signal and outer ear microphone signal;
detecting speech from the user;
interrupting application of the adaptation process upon detecting speech by the user;
restarting the application of the adaptation process once speech is no longer detected;
providing the denoised signal.

2. The method of claim 1, wherein the step of interrupting application of the adaptation process includes updating filter weights of the adaptive filter to values previous to the detection of speech by the user.

3. The method of claim 1, wherein the step of detecting speech from the user includes the sub-steps of:
computing filter weights of the adaptive filter;
upon detecting an increase in the filter weights for two consequent time indexes greater than a triggering threshold, providing an indication of detection of speech by the user.

4. The method of claim 3, wherein the triggering threshold is between 1 and 20 percent.

5. The method of claim 3, wherein the triggering threshold is between 6 and 7 percent.

6. The method of any of claims 1 to 5, wherein the estimated transfer function of the intra-aural device is estimated, while the user is wearing the intra-aural device, by:
generating white noise outside the ear of the user for at least two seconds;
simultaneously acquiring the in-ear microphone signal and the outer-ear microphone signal;
computing the estimated transfer function of the intra-aural device based on the simultaneously acquired in-ear microphone signal and outer-ear microphone signal.

7. The method of claim 6, wherein the white noise is at least 85 dB.

8. The method of any of claims 1 to 7, wherein the adaptive filter is a normalized least mean square adaptive filter.

9. The method of any of claims 1 to 8, further comprising the step of:
extending a bandwidth of the denoised signal in high frequencies using a non-linear bandwidth extension process previous to providing the denoised signal.

10. The method of claim 9, wherein the bandwidth is extended in a range from 1.8 kHz to 4 kHz.

11. The method of claim 9, wherein extending the bandwidth of the denoised signal includes the sub-steps of:
upsampling the denoised signal by a factor of two;
applying a whitening filter to the upsampled denoised signal using linear predictive coding coefficients;
cubing the filtered upsampled denoised signal;
applying a high pass third order filter to the cubed filtered upsampled denoised signal;
applying a low pass third order filter to the upsampled denoised signal;

summing a high passed signal and a low passed signal;
applying a band pass fourth order filter to the summed signals;
downsampling a band passed signal by a factor of two.

12. The method of claim 10, wherein high pass and low pass third order filters are at 1.8 kHz.

13. The method of either of claim 10 or 11, wherein the band pass fourth order filter is a Linkwitz-Riley filter at 160 Hz and 3.5 kHz.

14. A device for enhancing speech generated from bone and tissue conduction of a user in a noisy environment, the device comprising:
an intra-aural unit adapted to be positioned into an ear of the user, the intra-aural unit having an in-ear microphone adapted to be in fluid communication with an outer ear canal of the ear and an outer ear microphone adapted to be in fluid communication with an environment outside the ear;
a transmitter;
a processing unit operatively connected to the in-ear microphone to receive an internal signal therefrom, to the outer-ear microphone to receive an external signal therefrom and to the transmitter, the processing unit having an associated memory comprising instructions stored thereon, that when executed on the processor perform the steps of:
acquiring the internal signal from the in-ear microphone;
acquiring the external signal from the outer-ear microphone;
applying an adaptive filter to the acquired in-ear microphone signal to produce a denoised signal, the adaptive filter:
being initialized by an estimated transfer function of the intra-aural device based on the outer-ear microphone signal and the in-ear microphone signal;
having an adaptation process continuously adjusting the estimated transfer function using the acquired in-ear microphone signal and outer ear microphone signal;
detecting speech from the user;
interrupting application of the adaptation process upon detecting speech by the user;
restarting the application of the adaptation process once speech is no longer detected; and
providing the denoised signal via the transmitter.

15. The device of claim 14, wherein the intra-aural unit is inflatable, compressible or custom molded to the ear of the user.

16. The device of either of claim 14 or 15, wherein at least one of the transmitter and the processing unit is located inside the intra-aural unit.

17. The device of any of claims 14 to 16, further comprising a receiver and wherein the intra-aural unit further includes a loudspeaker.

18. The device of claim 17, wherein the receiver is located inside the intra-aural unit.

19. The device of claim 14, wherein when the processor performs the step of interrupting application of the adaptation process, the processor further performs the sub-steps of updating filter weights of the adaptive filter to values previous to the detection of speech by the user.

20. The device of any of claims 14 to 19, wherein when the processor performs the step of detecting speech from the user, the processor further performs the sub-steps of:
computing filter weights of the adaptive filter;
upon detecting an increase in the filter weights for two consequent time indexes greater than a triggering threshold, providing an indication of detection of speech by the user.

21. The device of any of claims 14 to 20, wherein the triggering threshold is between 1 and 20 percent.

22. The device of any of claims 14 to 20, wherein the triggering threshold is between 6 and 7 percent.

23. The device of any of claims 14 to 22, wherein the estimated transfer function of the intra-aural device is estimated, while the user is wearing the intra-aural device, by:
generating white noise outside the ear of the user for at least two seconds;
simultaneously acquiring the in-ear microphone signal and the outer-ear microphone signal;
computing the estimated transfer function of the intra-aural device based on the simultaneously acquired in-ear microphone signal and outer-ear microphone signal.

24. The device of claim 23, wherein the white noise is at least 85 dB.

25. The device of any of claims 14 to 24, wherein the adaptive filter is a normalized least mean square adaptive filter.

26. The device of any of claims 14 to 25, wherein the processor further performs the steps of:
extending a bandwidth of the denoised signal in high frequencies using a non-linear bandwidth extension process previous to providing the denoised signal.

27. The device of claim 26, wherein the bandwidth is extended in the range from 1.8 kHz to 4 kHz.

28. The device of claim 26, wherein when the processor performs the step of extending the bandwidth of the denoised signal, the processor further performs the sub-steps of:
upsampling the denoised signal by a factor of two;
applying a whitening filter to the upsampled denoised signal using linear predictive coding coefficients;
cubing the filtered upsampled denoised signal;
applying a high pass third order filter to the cubed filtered upsampled denoised signal;
applying a low pass third order filter to the upsampled denoised signal;
summing a high passed signal and a low passed signal;
applying a band pass fourth order filter to the summed signals;
downsampling a band passed signal by a factor of two.

29. The device of claim 28, wherein high pass and low pass third order filters are at 1.8 kHz.

30. The device of either of claim 28 or 29, wherein the band pass fourth order filter is a Linkwitz-Riley filter at 160 Hz and 3.5 kHz.

31. A method for detecting speech of a user of an intra-aural device in a noisy environment, the intra-aural device having an in-ear microphone adapted to be in fluid communication with an outer-ear ear canal of the user and an outer-ear microphone adapted to be in fluid communication with an environment outside the ear, the method comprising the steps of:
acquiring a signal from the in-ear microphone;
acquiring a signal from the outer-ear microphone;
applying an adaptive filter to the acquired in-ear microphone signal, the adaptive filter being initialized by an estimated transfer function of the intra-aural device based on the outer-ear microphone signal and the in-ear microphone signal;

computing filter weights of the adaptive filter;
upon detecting an increase in the filter weights for two consequent time indexes greater than a triggering threshold, providing an indication of detection of speech by the user.

32. The method of claim 31, wherein the adaptive filter is a normalized least mean square adaptive filter.

33. The method of either of claim 31 or 32, wherein the triggering threshold is between 1 and 20 percent.

34. The method of either of claim 31 or 32, wherein the triggering threshold is between 6 and 7 percent.

35. The method of any of claims 31 to 34, wherein the estimated transfer function of the intra-aural device is estimated, while the user is wearing the intra-aural device, by:
generating white noise outside the ear of the user for at least two seconds;
simultaneously acquiring the in-ear microphone signal and the outer-ear microphone signal;
computing the estimated transfer function of the intra-aural device based on the simultaneously acquired in-ear microphone signal and outer-ear microphone signal.

36. A device for detecting speech of a user of an intra-aural device in a noisy environment, the device comprising:
an intra-aural unit adapted to be positioned into an ear of the user, the intra-aural unit having an in-ear microphone adapted to be in fluid communication with an outer ear canal of the ear and an outer ear microphone adapted to be in fluid communication with an environment outside the ear;
a transmitter;
a processing unit operatively connected to the in-ear microphone to receive an internal signal therefrom, to the outer-ear microphone to receive an external signal therefrom and to the transmitter, the processing unit having an associated memory comprising instructions stored thereon, that when executed on the processor perform the steps of:
acquiring a signal from the in-ear microphone;
acquiring a signal from the outer-ear microphone;
applying an adaptive filter to the acquired in-ear microphone signal, the adaptive filter being initialized by an estimated transfer function of the intra-aural device based on the outer-ear microphone signal and the in-ear microphone signal;
computing filter weights of the adaptive filter;
upon detecting an increase in the filter weights for two consequent time indexes greater than a triggering threshold, providing an indication of detection of speech by the user via the transmitter.

37. The device of claim 36, wherein the adaptive filter is a normalized least mean square adaptive filter.

38. The device of either of claim 36 or 37, wherein the triggering threshold is between 1 and 20 percent.

39. The device of either of claim 36 or 37, wherein the triggering threshold is between 6 and 7 percent.

40. The device of any of claims 36 to 39, wherein the estimated transfer function of the intra-aural device is estimated, while the user is wearing the intra-aural device, by:
generating white noise outside the ear of the user for at least two seconds;
simultaneously acquiring the in-ear microphone signal and the outer-ear microphone signal;
computing the estimated transfer function of the intra-aural device based on the simultaneously acquired in-ear microphone signal and outer-ear microphone signal.

* * * * *